United States Patent
Webb et al.

(10) Patent No.: US 7,806,932 B2
(45) Date of Patent: Oct. 5, 2010

(54) SPINAL IMPLANT

(75) Inventors: Scott A. Webb, Largo, FL (US);
Anthony P. Moreno, Tarpon Springs, FL (US); Margaret E. Mitchell, Cedar Park, TX (US); Aaron C. Smith, Arlington, TN (US)

(73) Assignee: Zimmer Spine, Inc., Minneapolis, MN (US)

( * ) Notice: Subject to any disclaimer, the term of this patent is extended or adjusted under 35 U.S.C. 154(b) by 862 days.

(21) Appl. No.: 10/633,371

(22) Filed: Aug. 1, 2003

(65) Prior Publication Data

US 2005/0027360 A1 Feb. 3, 2005

(51) Int. Cl.
*A61F 2/44* (2006.01)
(52) U.S. Cl. .................................. 623/17.11
(58) Field of Classification Search ... 623/17.11–17.16; 606/246
See application file for complete search history.

(56) References Cited

U.S. PATENT DOCUMENTS

| | | | |
|---|---|---|---|
| 3,867,728 A * | 2/1975 | Stubstad et al. ......... | 623/17.16 |
| 4,743,256 A | 5/1988 | Brantigan | |
| 4,768,787 A | 9/1988 | Shira | |
| 4,834,757 A | 5/1989 | Brantigan | |
| 4,878,915 A | 11/1989 | Brantigan | |
| 4,964,641 A | 10/1990 | Miesch et al. | |
| 5,019,081 A | 5/1991 | Watanabe | |
| 5,171,278 A | 12/1992 | Pisharodi | |
| 5,192,327 A | 3/1993 | Brantigan | |
| 5,306,307 A | 4/1994 | Senter et al. | |
| 5,424,772 A | 6/1995 | Brantigan | |
| 5,429,863 A | 7/1995 | McMillin | |
| 5,443,514 A | 8/1995 | Steffee | |
| 5,526,664 A | 6/1996 | Vetter | |
| 5,609,635 A | 3/1997 | Michelson | |
| 5,653,763 A | 8/1997 | Errico et al. | |

(Continued)

FOREIGN PATENT DOCUMENTS

DE 29901611 6/1999

(Continued)

OTHER PUBLICATIONS

PCT/US2004/023721 {PCT International Search Report)—Intl Filing Date Jul. 22, 2004.

(Continued)

*Primary Examiner*—Eduardo C Robert
*Assistant Examiner*—David Comstock
(74) *Attorney, Agent, or Firm*—Sprinkle IP Law Group

(57) ABSTRACT

A spinal implant may be used to stabilize a portion of a spine. The implant may promote bone growth between adjacent vertebrae that fuses the vertebrae together. An implant may include an opening through a height of a body of the implant. The body of the implant may include curved sides. A top and/or a bottom of the implant may include protrusions that contact and/or engage vertebral surfaces to prevent backout of the implant from the disc space. A variety of instruments may be used to prepare a disc space and insert an implant. The instruments may include, but are not limited to, a distractor, a rasp, and one or more guides. The implant and instruments may be supplied in an instrument kit.

50 Claims, 8 Drawing Sheets

U.S. PATENT DOCUMENTS

| | | | |
|---|---|---|---|
| 5,713,899 A | 2/1998 | Marnay et al. | |
| 5,716,415 A | 2/1998 | Steffee | |
| 5,717,006 A | 2/1998 | Daculsi et al. | |
| 5,733,290 A | 3/1998 | McCue et al. | |
| 5,766,252 A * | 6/1998 | Henry et al. | 623/17.16 |
| 5,769,897 A | 6/1998 | Harle | |
| 5,814,084 A | 9/1998 | Grivas et al. | |
| 5,836,958 A | 11/1998 | Ralph | |
| 5,888,227 A * | 3/1999 | Cottle | 623/17.16 |
| 5,918,821 A | 7/1999 | Grooms et al. | |
| 5,984,922 A | 11/1999 | McKay | |
| 5,989,289 A | 11/1999 | Coates et al. | |
| 6,025,538 A | 2/2000 | Yaccarino, III | |
| 6,113,639 A | 9/2000 | Ray et al. | |
| 6,143,032 A * | 11/2000 | Schafer et al. | 623/17.11 |
| 6,143,033 A | 11/2000 | Paul et al. | |
| 6,159,211 A | 12/2000 | Boriani et al. | |
| 6,174,311 B1 * | 1/2001 | Branch et al. | 606/61 |
| 6,200,347 B1 | 3/2001 | Anderson et al. | |
| 6,224,607 B1 | 5/2001 | Michelson | |
| 6,241,770 B1 | 6/2001 | Michelson | |
| 6,245,108 B1 * | 6/2001 | Biscup | 623/17.11 |
| 6,277,149 B1 | 8/2001 | Boyle et al. | |
| 6,290,724 B1 | 9/2001 | Marino | |
| 6,294,187 B1 | 9/2001 | Boyce et al. | |
| 6,346,123 B1 | 2/2002 | McKay | |
| 6,468,311 B2 * | 10/2002 | Boyd et al. | 623/17.16 |
| 6,517,544 B1 | 2/2003 | Michelson | |
| 6,530,956 B1 * | 3/2003 | Mansmann | 623/18.11 |
| 6,537,589 B1 | 3/2003 | Chae et al. | |
| 6,579,318 B2 * | 6/2003 | Varga et al. | 623/17.11 |
| 6,599,294 B2 | 7/2003 | Fuss et al. | |
| 6,599,295 B1 | 7/2003 | Tornier | |
| 6,613,089 B1 * | 9/2003 | Estes et al. | 623/17.11 |
| 6,648,915 B2 | 11/2003 | Sazy | |
| 6,682,534 B2 | 1/2004 | Patel et al. | |
| 6,699,288 B2 | 3/2004 | Moret | |
| 6,719,794 B2 * | 4/2004 | Gerber et al. | 623/17.11 |
| 6,764,491 B2 | 7/2004 | Frey et al. | |
| 6,830,570 B1 * | 12/2004 | Frey et al. | 623/17.16 |
| 6,852,127 B2 | 2/2005 | Varga et al. | |
| 6,974,480 B2 | 12/2005 | Messerli et al. | |
| 7,060,073 B2 | 6/2006 | Frey et al. | |
| 7,500,991 B2 | 3/2009 | Bartish, Jr. et al. | |
| 2001/0021853 A1 | 9/2001 | Heckele et al. | |
| 2002/0077700 A1 * | 6/2002 | Varga et al. | 623/17.11 |
| 2002/0087212 A1 * | 7/2002 | James et al. | 623/17.11 |
| 2002/0143400 A1 * | 10/2002 | Biscup | 623/17.11 |
| 2002/0165612 A1 | 11/2002 | Gerber et al. | |
| 2003/0069586 A1 | 4/2003 | Errico et al. | |
| 2003/0100950 A1 * | 5/2003 | Moret | 623/17.16 |
| 2004/0127990 A1 * | 7/2004 | Bartish et al. | 623/17.11 |
| 2005/0004671 A1 * | 1/2005 | Ross et al. | 623/17.11 |
| 2005/0096745 A1 | 5/2005 | Andre | |
| 2006/0095043 A1 | 5/2006 | Martz et al. | |
| 2006/0229627 A1 | 10/2006 | Hunt et al. | |
| 2006/0241761 A1 | 10/2006 | Gately | |
| 2007/0142843 A1 | 6/2007 | Dye | |
| 2007/0225726 A1 | 9/2007 | Dye | |
| 2007/0225808 A1 | 9/2007 | Warnick | |
| 2008/0009880 A1 | 1/2008 | Warnick et al. | |
| 2008/0027544 A1 | 1/2008 | Melkent | |
| 2008/0065082 A1 | 3/2008 | Chang et al. | |
| 2008/0077150 A1 | 3/2008 | Nguyen | |
| 2008/0077241 A1 | 3/2008 | Nguyen | |
| 2008/0091211 A1 | 4/2008 | Gately | |

FOREIGN PATENT DOCUMENTS

| | | |
|---|---|---|
| DE | 19903762 C1 | 11/2000 |
| FR | 2736537 | 1/1997 |
| JP | 09122160 | 5/1997 |
| JP | 2002503135 T | 1/2002 |
| JP | 3692169 | 6/2005 |
| WO | WO 98/17209 | 4/1998 |
| WO | WO 98/56319 | 12/1998 |
| WO | WO 00/44288 | 8/2000 |
| WO | WO 02/17823 | 3/2002 |

OTHER PUBLICATIONS

International Preliminary Report on Patentability for PCT/US2004/023721 dated Feb. 6, 2006, 12 pgs.

Examination Report issued Jul. 3, 2009 for Australian Patent Application No. 2004261160, 3 pages.

Captiva Spine Receives 510(k) Clearance for its Proprietary Lumbar Interbody Fusion Device, the Pivotec, Captiva Spine, Inc., Jupiter, FL, Dec. 9, 2009, at http://www.pr.com/press-release/197472, 2 pgs.

Office Action issued in U.S. Appl. No. 11/257,745 mailed Dec. 11, 2008, 7 pgs.

Office Action issued in U.S. Appl. No. 11/257,745 mailed Oct. 2, 2009, 7 pgs.

Office Action issed in Canadian Patent Application No. 2,534,357 mailed Feb. 11, 2010, 3 pgs.

Office Action and English Translation issued in Japanese Patent Application No. 2006-521937, issued Jan. 14, 2010, mailed Jan. 19, 2010, 8 pgs.

Examination Report issued in Australian Patent Application No. 2004261160, mailed Apr. 6, 2010, 1 page.

Japanese Patent Office Action issued in Japanese Patent Application No. 2006-521937, mailed Jun. 1, 2010, with English translation, 6 pgs.

\* cited by examiner

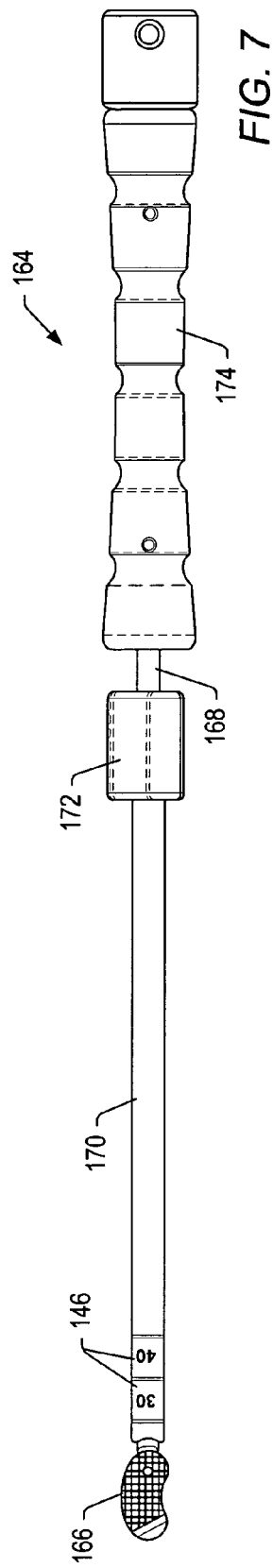
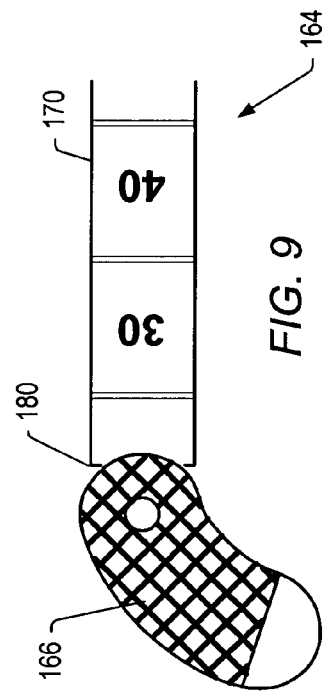
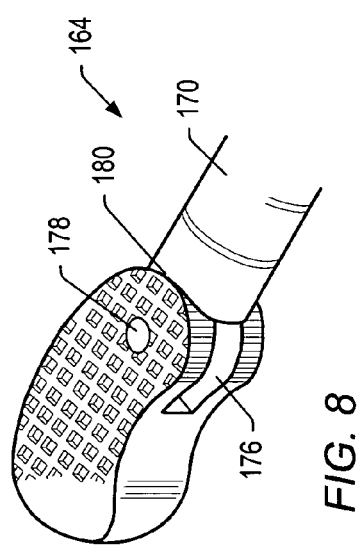

SPINAL IMPLANT

BACKGROUND

1. Field of Invention

The present invention generally relates to the field of medical devices. Some embodiments of the invention relate to spinal implants inserted in patients during surgical procedures and to instruments used to insert the implants. Some embodiments of the invention relate to instruments for preparing a space for an implant. Other embodiments of the invention relate to methods for positioning an implant during a surgical procedure.

2. Description of Related Art

An intervertebral disc may degenerate. Degeneration may be caused by trauma, disease, and/or aging. An intervertebral disc that becomes degenerated may have to be partially or fully removed from a spinal column. Partial or full removal of an intervertebral disc may destabilize the spinal column. Destabilization of a spinal column may result in alteration of a natural separation distance between adjacent vertebrae. Maintaining the natural separation between vertebrae may prevent pressure from being applied to nerves that pass between vertebral bodies. Excessive pressure applied to the nerves may cause pain and/or nerve damage. During a spinal fixation procedure, a spinal implant may be inserted in a space created by the removal or partial removal of an intervertebral disc between adjacent vertebrae. The spinal implant may maintain the height of the spine and restore stability to the spine. Bone growth may fuse the implant to adjacent vertebrae.

A spinal implant may be inserted during a spinal fixation procedure using an anterior, lateral, posterior, or transverse spinal approach. A discectomy may be performed to remove or partially remove a defective or damaged intervertebral disc. The discectomy may create a space for a spinal implant. The amount of removed disc material may correspond to the size and type of spinal implant to be inserted.

Spinal surgery may be complex due in part to the proximity of the spinal cord and/or the cauda equina. Preparation instruments and spinal implants may need to be carefully inserted to avoid damage to nerve tissue. Alignment and spacing of a spinal implant that is to be inserted into a patient may be determined before surgery. Achieving the predetermined alignment and spacing during surgery may be important to achieve optimal fusion of adjacent vertebrae.

Bone graft and/or bone implants may be used to promote bone growth that will fuse vertebrae together. Bone graft may be autogenic bone, allogenic bone, synthetic material, xenogenic bone or combinations thereof. Autogenic bone is bone obtained from another location of a patient. Allogenic bone is bone derived from the same species as the patient. Xenogenic bone is bone derived from a species other than that of the patient. Implants may be formed of metal, polymers, ceramics, inorganic compositions, autogenic bone, allogenic bone, xenogenic bone, or combinations thereof.

Spinal implants are described in U.S. Pat. No. 5,653,763 to Errico et al.; U.S. Pat. No. 5,713,899 to Marney et al.; U.S. Pat. No. 6,143,033 to Paul et al.; U.S. Pat. No. 6,245,108 to Biscup; and U.S. Pat. No. 5,609,635 to Michelson, all of which are incorporated by reference herein as if fully set forth herein.

SUMMARY

A spinal implant may be used to provide stability and promote fusion of adjacent vertebrae. The implant may be used in conjunction with a spinal stabilization device such as a bone plate or rod-and-fastener stabilization system. The implant may establish a desired separation distance between vertebrae. The implant may promote bone growth between adjacent vertebrae that fuses the vertebrae together. An instrumentation kit may include instruments and implants necessary for insertion of an implant in a patient.

Implants may be constructed of biocompatible materials sufficiently strong to maintain spinal distraction. Implants may include, but are not limited to, allograft bone, xenograft bone, autograft bone, metals, ceramics, inorganic compositions, polymers, or combinations thereof. If the implant is not made of bone, surfaces of the implant that contact bone may be treated to promote fusion of the implant to the bone. Treatment may include, but is not limited to, applying a hydroxyapatite coating on contact surfaces, spraying a titanium plasma on contact surfaces, and/or texturing the contact surfaces by scoring, peening, implanting particles in the surfaces, or otherwise roughening the surfaces.

In some embodiments, an implant may include an opening that extends through a height of the implant. The opening may have a regular shape or an irregular shape. Bone graft may be placed in the opening. The bone graft may be autogenic bone graft, allogenic bone graft, xenogenic bone graft, and/or synthetic bone graft. Some implant embodiments may be constructed from allogenic bone, such as cortical bone from a femur, tibia, or other large bone. In some embodiments, an implant may be formed from one or more pieces of allograft bone cut to a desired shape.

In certain embodiments, sides of an implant may be shaped to increase contact between an implant and adjacent vertebrae. Increasing contact of an implant with adjacent vertebrae may inhibit movement of the implant after insertion. An increased contact area between an implant and adjacent vertebrae may promote bone growth between adjacent vertebrae. In some embodiments, one or more sides of an implant may be curved. One or more curved sides of an implant may allow the implant to be maneuvered in a disc space during insertion of the implant. The curvature of a side may approximate a curvature of an anterior side of a vertebra adjacent to which the implant is inserted.

In certain embodiments, an implant may have one or more passages extending from an outer side of a body of the implant to an inner side of the body. The passages may communicate with a central opening in the implant. The passages may facilitate insertion of packing material in the central opening. In certain embodiments, one or more projections may extend from an inner side of the body into the central opening. The projections may be substantially the same height as the implant. Dimensions of a projection may be chosen to strengthen the implant without significantly decreasing the size of the central opening.

In some embodiments, an outer side of an implant may include a groove near the proximal end and/or the distal end of the body. The groove may be designed to receive an instrument to facilitate insertion of the implant in an intervertebral disc space.

A top and/or a bottom of an implant may include protrusions. The protrusions may engage vertebral surfaces. Protrusions may inhibit backout of the implant from the vertebrae. The protrusions may form a radial pattern. In some embodiments, one or more protrusions may have the same height, width, and/or spacing. In certain embodiments, one or more protrusions may have different heights, widths and/or spacing.

Instruments may be used to prepare a space for an implant between adjacent vertebrae. An instrument may be used to insert an implant in a prepared space. Instruments may be supplied to a surgeon or surgical team in an instrument set. An instrument set may include one or more implants for use during an insertion procedure. An instrument set may include implants of various sizes and/or lordotic angles to allow selection of an implant to suit a patient during surgery.

An instrumentation set may include one or more distractors. In some embodiments, a distractor may be fixed-tip distractor. A tip of the distractor may include a narrow dimension and a wide dimension. In some embodiments, one or more surfaces of a tip of a distractor may be convex. A distractor tip with a convex surface may reduce trauma to a surgical site during distraction of vertebrae. In certain embodiments, a tip of the distractor may include cutting surfaces.

An instrumentation set may include a rasp to abrade a vertebral surface before insertion of an implant in a disc space. In some embodiments, a rasp may include an end member pivotably coupled to an inner shaft of the rasp. An angle of the end member relative to the inner shaft may be varied as the rasp is moved through the disc space.

An instrumentation set may include an implant inserter. The implant inserter may be used to grasp sides of an implant. After insertion of the implant, the implant may be released from the inserter without the application of significant rotational forces to the implant. The implant inserter may have a low profile that allows for visualization of the implant and surrounding area during insertion of the implant.

A discectomy may be performed to establish a disc space between vertebrae. The disc space may be prepared for implant insertion by distraction of adjacent vertebrae. In some embodiments, a rasp may be inserted in a disc space to remove osteophytes and/or to smooth the vertebral surfaces. Abrasion of the vertebral surfaces may promote contact between the implant and the vertebrae. An angle of an end member of the rasp may be adjusted as the rasp is moved through the disc space to abrade the vertebrae. The rasp may be removed from the disc space and a first guide may be inserted in the disc space. An implant coupled to an implant inserter may be placed proximate the first guide and guided into the disc space using a transverse approach along the surface of the first guide. The implant may be removed from the implant inserter. A second guide may be inserted in the disc space near the proximal end of the implant. The first and second guides may be used together to position the implant in the disc space. The first and second guides may be removed from the disc space.

BRIEF DESCRIPTION OF THE DRAWINGS

Advantages of the present invention will become apparent to those skilled in the art with the benefit of the following detailed description and upon reference to the accompanying drawings in which:

FIG. 7 depicts a front view of an embodiment of a rasp.

FIG. 8 depicts a perspective view of an embodiment of an end member of a rasp.

FIG. 9 depicts a front view of an embodiment of a pivoted end member of a rasp.

Figure 1:
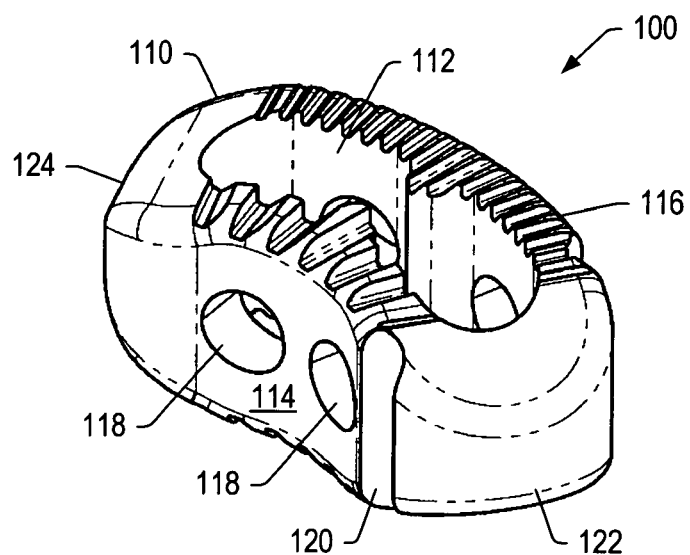
FIG. 1 depicts a perspective view of an embodiment of a spinal implant.

While the invention is susceptible to various modifications and alternative forms, specific embodiments thereof are shown by way of example in the drawings and will herein be described in detail. The drawings may not be to scale. It should be understood that the drawings and detailed description are not intended to limit the invention to the particular form disclosed, but on the contrary, the intention is to cover all modifications, equivalents, and alternatives falling within the spirit and scope of the present invention as defined by the appended claims.

DETAILED DESCRIPTION

An intervertebral disc implant may be used to stabilize a portion of a spine. The disc implant may replace all or a portion of an intervertebral disc that has degenerated due to natural wear, trauma, or disease. The implant may restore a normal separation distance between adjacent vertebrae and promote fusion of the vertebrae.

FIG. 1 depicts a perspective view of implant 100. Implant 100 may include body 110. Body 110 may include opening 112. Opening 112 may extend completely or partially through a height of body 110. A cross-sectional shape of opening 112 may be, but is not limited to, circular, oval, square, rectangular, or irregular. In certain embodiments, opening 112 may be kidney shaped.

Body 110 of implant 100 may include posterior side 114 and anterior side 116. Sides 114, 116 of implant 100 may be curved. In some embodiments, the curvature of posterior side 114 may be substantially the same as the curvature of anterior side 116. In some embodiments, the curvature of posterior side 114 may be different than the curvature of anterior side 116. In some embodiments, posterior side 114 may have a smaller radius of curvature than anterior side 116. A curvature of anterior side 116 may approximate a curvature of an anterior side of a vertebra adjacent to which the implant is inserted. Curvature of posterior side 114 may allow implant 100 to be maneuvered in the disc space during transverse insertion of the implant.

In certain embodiments, body 110 of implant 100 may have one or more passages extending through sides 114, 116 substantially perpendicular to opening 112 of the body. A cross-sectional shape of one of the passages may be, but is not limited to, circular, oval, square, rectangular, or irregular. FIG. 1 depicts sides 114, 116 with passages 118. Passages 118 may communicate with opening 112. Passages 118 may facilitate insertion of packing material in opening 112. Passages 118 may promote increased blood flow between the packing material and vertebrae adjacent to implant 100. In some embodiments, the packing material may be a preformed insert that slides into opening 112.

Sides 114, 116 may include groove 120 near proximal end 122 and/or distal end 124 of body 110. Groove 120 may be designed to receive an instrument (e.g., an implant inserter) to facilitate insertion of implant 100 in an intervertebral disc space. Groove 120 may facilitate insertion of implant 100 using, for example, an anterior approach, a posterior approach, or a transverse approach.

Figure 2:
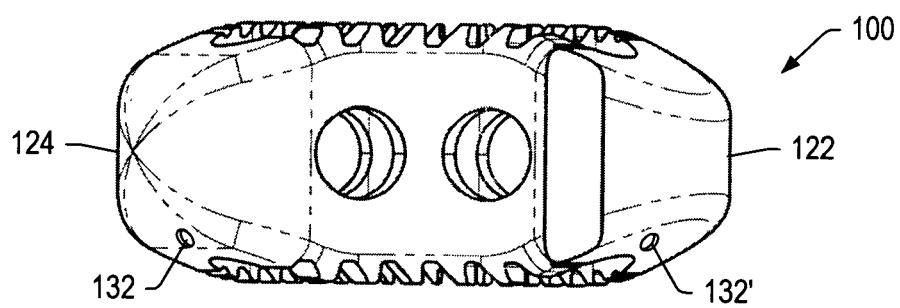
FIG. 2 depicts a view of the posterior side of an embodiment of a spinal implant.

FIG. 2 depicts a view of a posterior side of implant 100. Distal end 124 of body 110 may be tapered and/or curved. Tapered and/or curved surfaces of distal end 124 may facilitate insertion of implant 100 in a disc space. In some embodiments, distal end 124 may not be tapered and/or curved. Proximal end 122 of body 110 may be blunt and/or rounded. In some embodiments, proximal end 122 of body 110 may have a substantially flat surface. A guide (e.g., a tamp) or other insertion instrument may be placed against proximal end 122 during insertion of implant 100 in a disc space using a transverse insertion procedure. Proximal end 122 of implant 100 may be engraved or otherwise marked with indicia to allow a user to identify an orientation of the implant and/or one or more properties of the implant.

Figure 3:
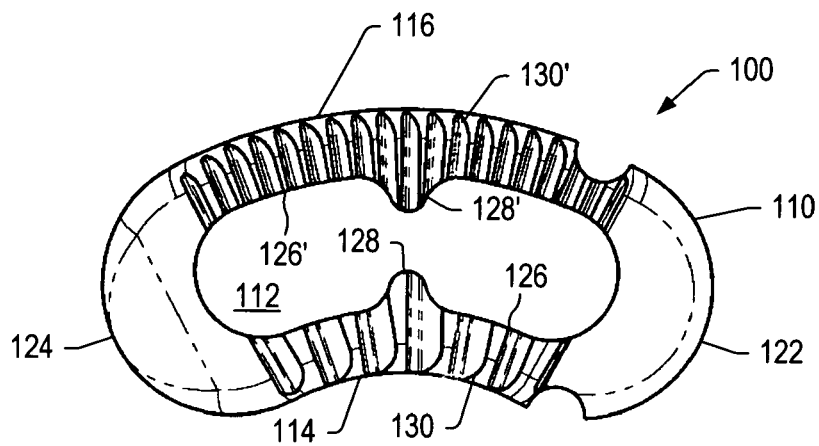
FIG. 3 depicts a top view of an embodiment of a spinal implant.

FIG. 3 depicts a top view of body 110. Surfaces 126, 126', which define opening 112 along sides 114, 116, may include one or more projections 128, 128'. In some embodiments, projections 128, 128' may be tapered. In certain embodiments, projections 128, 128' may be angled or rounded.

Projections 128, 128' may be located substantially equidistant from ends 122, 124. In some embodiments, projection 128 may be closer to proximal end 122 than projection 128'. In certain embodiments, projection 128 may be closer to distal end 124 than projection 128'. Projections 128, 128' may strengthen implant 100.

Top and/or bottom surfaces of implant 100 may include one or more protrusions 130, 130'. In some embodiments, one or more protrusions 130, 130' may penetrate vertebral bone. For example, an implant made of metal may include protrusions that are able to penetrate vertebral bone. In some embodiments, one or more protrusions 130, 130' may not penetrate vertebral bone. For example, an implant made of bone may include protrusions that are not able to penetrate vertebral bone. Protrusions 130, 130' may be blunt, rounded, symmetrically angled, asymmetrically angled, or pointed. The protrusions may inhibit backout of the implant from the disc space. Protrusions 130, 130' may form a radial pattern. In certain embodiments, protrusions 130, 130' may have a constant height, width, and/or spacing along a length of body 110. In other embodiments, one or more protrusions 130, 130' may have different heights, widths, and/or spacing. For example, a width of protrusions 130 may differ from a width of protrusions 130'. Heights of protrusions 130, 130' may decrease or increase toward ends 122, 124, of body 110. Spacing of protrusions 130, 130' may increase or decrease toward ends 122, 124 of body 110.

In some embodiments, protrusions 130 on posterior side 114 may be higher and/or larger than protrusions 130' on anterior side 116. Higher and/or larger protrusions on a posterior side may allow a greater load to be applied to posterior side 114 as implant 100 is inserted in a disc space. The greater load may facilitate proper rotation of the implant in the disc space during insertion.

As depicted in FIG. 3, in some embodiments, implant 100 may include coarse protrusions 130' near a posterior side of the implant and fine protrusions 130 near an anterior side of the implant. Coarse protrusions 130' may have greater height and/or spacing than fine protrusions 130. In some embodiments, an implant may include coarse protrusions near an anterior side of the implant and fine protrusions near a posterior side of the implant. In some embodiments, an implant may have the same type of protrusion (coarse, fine or intermediate) near the anterior side and posterior side.

In some embodiments, a top of an implant may have the same types of protrusions as a bottom of the implant. In some embodiments, the top of the implant may include different protrusion types than the bottom. For example, the top of the implant may include coarse protrusions near the posterior side, fine protrusions near the anterior side, and the implant bottom may include intermediate protrusions near both the anterior side and the posterior side.

In some embodiments, top and/or bottom surfaces of a spinal implant may be angled relative to each other to increase contact between the implant and vertebral surfaces after insertion. Angled top and/or bottom surfaces of an implant may help establish a desired orientation (i.e., a proper lordotic angle) between vertebrae that are to be fused together. Implants may be formed with different lordotic angles. In certain embodiments, a lordotic angle of an implant may be between about 0° and about 6°.

Various materials may be packed in an opening of a spinal implant. A size of an opening may facilitate insertion of materials without adversely affecting the structural integrity of the implant. Packing materials may include, but are not limited to, allograft bone, bone-void filler, graft extender material, medicine, human tissue, animal tissue, synthetic tissue, human cells, animal cells, synthetic cells, or combinations thereof. In some embodiments, packing material may facilitate fusion of adjacent vertebrae with an implant.

In certain embodiments, bone may be used to form a spinal implant. Bone used to form an implant may be, but is not limited to, cortical, allogenic, or xenogenic bone. In some embodiments, a portion or portions of an implant may be autogenic bone. In some embodiments, bone, or portions of bone, used to form an implant may be demineralized. Bone used to form a spinal implant may be processed in a frozen state. In some embodiments, bone used to form an implant may be processed in a freeze-dried state.

In some embodiments, a spinal implant may be constructed of biocompatible material sufficiently strong to maintain bone separation. An implant, or a portion of an implant, may be made of a bioabsorbable material. For example, portions of an implant may be made of a polyanhydride, an alpha polyester, and/or a polylactic acid-polyglycolic acid copolymer.

In certain embodiments, a spinal implant may include one or more inorganic compositions. For example, an implant may be made of monocalcium phosphate, biphasic calcium phosphate, β-tricalcium phosphate, calcium metal phosphate, calcium sulfate hemihydrate, hydroxyapatite, or combinations thereof. Metals for a calcium metal phosphate may include, but are not limited to, titanium, titanium alloys, and/or medical grade stainless steel. For example, an implant may be formed of greater than 90 wt % β-tricalcium phosphate. In some embodiments, an implant may be formed of greater than 99 wt % β-tricalcium phosphate. The use of inorganic compositions as biomaterial is described in U.S. Pat. No. 6,537,589 to Chae et al.; U.S. Pat. No. 6,346,123 to McKay; and U.S. Pat. No. 5,717,006 Daculsi et al., all of which are incorporated by reference as if fully set forth herein.

In some embodiments, a spinal implant may be constructed from bar stock or formed from moldable material of suitable strength to withstand pressure in a normal human spine. For example, an implant may be constructed from metals including, but not limited to, titanium, titanium alloys, and/or medical grade stainless steel. An implant may be molded or cut from materials including, but not limited to, polyether ether ketone (PEEK), carbon fiber reinforced PEEK, and other polymers.

In certain embodiments, a spinal implant and/or outer surfaces of the implant that contact a vertebra may be made of a material other than bone. A surface of an implant that contacts a vertebra may be treated to enhance osseointegration of the implant with the vertebra. The surface may include protrusions that extend into the vertebra. The surface may include a hydroxyapatite coating, a titanium plasma spray coating, and/or texturing. Texturing may be used to modify the surface of an implant to reduce expulsion and provide stability. Texturing may be provided by many different methods, such as, but not limited to, sanding the surface, forming grooves in the surface, shot peening the surface, scoring the surface using an electrical discharge process, and/or embedding hard particles in the surface. In some embodiments, an outer surface of an implant formed of bone may be textured.

In some cases, X-rays may be used to monitor spinal fusion in a patient. Some implant embodiments (e.g., PEEK implants) are substantially transparent to X-rays. X-ray detection of an implant formed of X-ray transparent material may be facilitated by including X-ray sensitive material in the implant. FIG. 2 depicts implant 100 with openings 132 for X-ray sensitive material. In an embodiment, tantalum wire (e.g., 1 mm in length) may be inserted into one or more openings 132 of implant 100 before implantation. In some embodiments, X-ray sensitive material may be located near an anterior side of the implant adjacent to a caudal (or cephalic) surface of the implant. X-ray sensitive material may also be located near a posterior side of the implant adjacent to a cephalic (or caudal) surface of the implant. The use of X-ray sensitive material in an implant may allow a location of the implant to be visualized after insertion using X-ray imaging.

Bone growth that fuses vertebrae together through an implant may be monitored subsequent to an implant insertion procedure. Bone growth in an implant that is not X-ray transparent (e.g., a metallic implant) may be monitored in a passage or an opening of the implant. For example, an X-ray image may indicate the presence, absence, and/or density of bone in passages 118 of implant 100.

X-ray and/or other imaging techniques may be used to determine a height and/or lordotic angle of an implant suitable for an implant insertion procedure. Implants that will provide the desired height and/or lordotic angle may be included with an instrumentation set for the implant insertion procedure. Implants with various heights and/or lordotic angles may be included with an instrumentation set to allow a range of options during a surgical procedure.

An instrumentation set may include instruments used to insert an implant in a disc space. Instruments used during implant insertion may allow positioning and/or manipulation of an implant to be affected from above an incision in a patient. The instruments may allow simple, efficient, and safe insertion of an implant. In some embodiments, an implant may be inserted in a disc space between adjacent vertebrae. In certain embodiments, an implant may be inserted in a space formed between two portions of a bone to extend the length of the bone. The instruments may allow implant insertion through a relatively small incision in a patient, while maintaining ample visibility of the surgical site, implant, and instruments during the procedure.

An instrumentation set for a spinal implant insertion procedure may include various instruments for distraction, disc preparation, and implantation. The distraction instruments may include fixed-tip and/or removable-tip distractors. Disc preparation instruments may include, but are not limited to, cutting distractors, rasps, curettes, rongeurs, chisels, and/or retractors. Implantation instruments may include implant inserters, mallets, one or more guides, and/or funnels.

Figure 4:
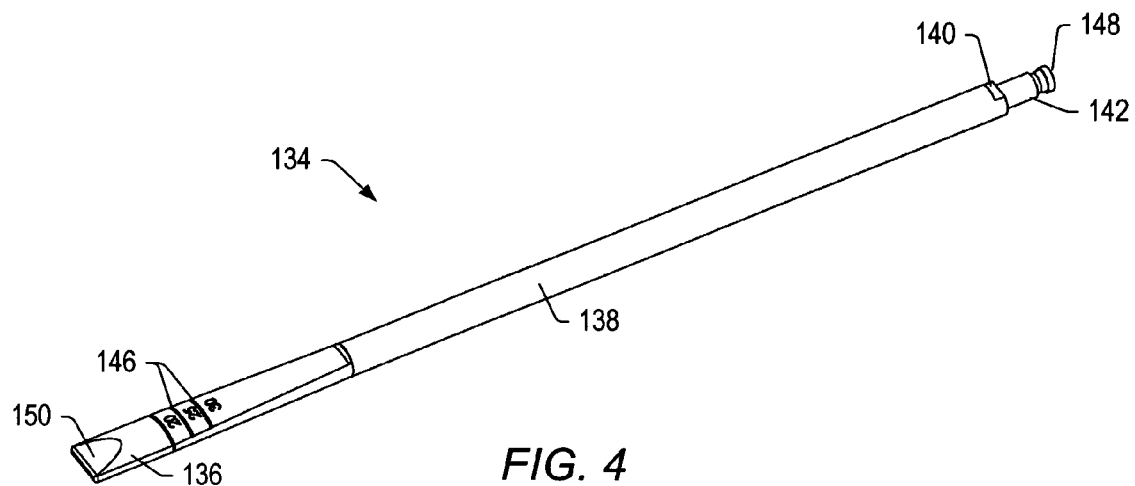
FIG. 4 depicts a perspective view of an embodiment of a fixed-tip distractor.

FIG. 4 depicts an embodiment of fixed-tip distractor 134. Distractor 134 may be used to separate vertebrae during an insertion procedure. Distractor 134 may include tip 136 and shaft 138. Tip 136 may be fixed to shaft 138. Shaft 138 may include indicia 146. Indicia 146 may indicate an insertion depth of tip 136 in a disc space. Shaft 138 may include flat 140 and connector 142. End 148 of connector 142 may have a cross-sectional shape similar to that of shaft 138. In some embodiments, end 148 may be a collar coupled to connector 142. Connector 142 may have a cross-sectional shape that is substantially the same as, but slightly smaller than, a cross-sectional shape of an opening in a removable handle. A removable handle (e.g., a T-handle) may fit over connector 142 and mate with flat 140 such that rotation of the handle results in rotation of tip 136. In some embodiments, shaft 138 may include a release and a detent that couples with an indention of a removable handle.

Figure 5:
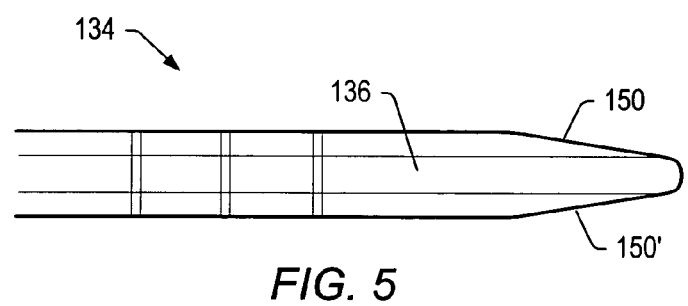
FIG. 5 depicts a side view of an embodiment of a fixed-tip distractor.

FIG. 5 depicts a side view of tip 136 of distractor 134. In some embodiments, tip 136 may have a narrow dimension and a wide dimension. The narrow dimension may be substantially perpendicular to the wide dimension. Surfaces 150, 150' may define the narrow dimension of tip 136. Surface 150 may taper toward surface 150'. In some embodiments, surface 150' may taper toward surface 150. The distal end of tip 136 may narrow progressively, such that the distal end of the tip is the narrowest portion of the tip.

Figure 6A:
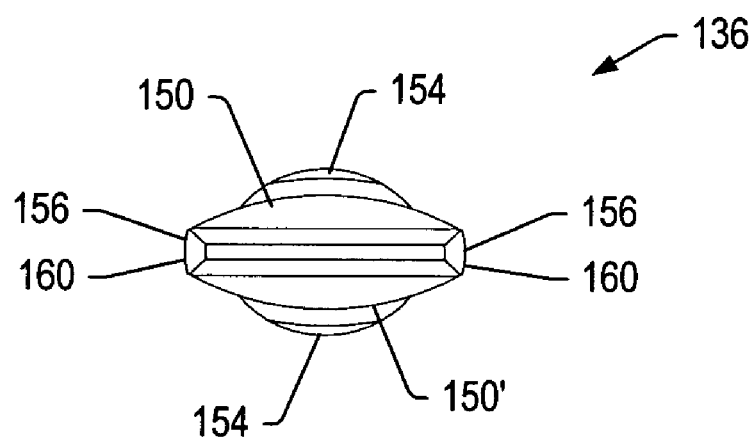
FIGS. 6A and 6B depict end views of embodiments of a fixed-tip distractor.

FIG. 6A depicts an end view of tip 136 of a distractor. Tip 136 may include curved surfaces 154. Curved surfaces 154 may be proximate tapered surfaces 150, 150'. A tip with a curved surface may rotate more easily in a disc space than a tip with a flat surface, thereby reducing trauma to the patient.

Figure 6B:
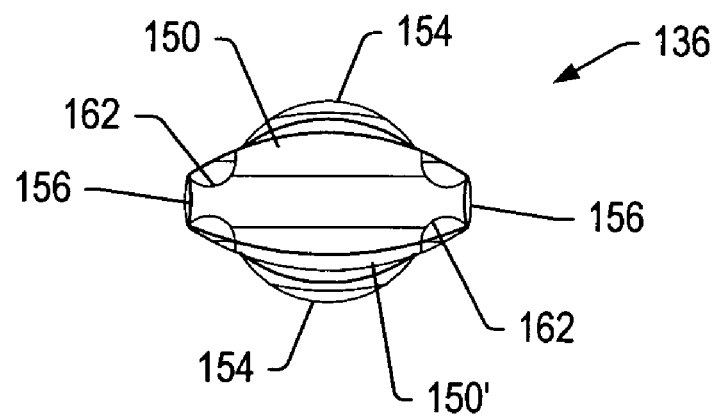

Surfaces 156 of tip 136 may define a wide dimension of tip 136. The wide dimension may be substantially constant along a length of the tip. The wide dimension may correspond to the desired separation distance to be established by the distractor between adjacent vertebrae. The desired separation distance may be, for example, 6 mm, 7 mm, 8 mm, 9 mm, 10 mm, 11 mm, 12 mm, or 13 mm. Edges 160 of tip 136 may be rounded to facilitate rotation of the tip between vertebrae. In some embodiments, tip 136 may be used to sever tissue (e.g., disc tissue). As depicted in FIG. 6B, tip 136 may include cutting surfaces 162 for severing tissue.

A removable handle may be may attached to shaft 138 of distractor 134. The handle may be coupled substantially parallel to the wide dimension of tip 136. The handle may be oriented perpendicular to a patient's spinal column, such that the narrow dimension of the tip is substantially perpendicular to the spinal column. The handle may be rotated approximately 90°, such that the handle and the wide dimension of tip 136 are substantially aligned with the spinal column. The wide portion of tip 136 may establish a desired separation distance between vertebrae. After distraction of the vertebrae, the handle may be removed from shaft 138.

Vertebral surfaces may require preparation before insertion of an implant in a disc space. Vertebral surfaces may be abraded to remove osteophytes and/or to smooth rough surfaces. An instrument such as a rasp may be inserted in an intervertebral disc space from a posterior or transverse approach to abrade vertebral surfaces.

FIG. 7 depicts a front view of rasp 164 that may be used to abrade vertebral surfaces. Rasp 164 may include end member 166, inner shaft 168, outer shaft 170, locking member 172, and handle 174. End member 166 may couple to inner shaft 168. Inner shaft 168 may be coupled to handle 174. Outer shaft 170 may have a cross-sectional shape substantially the same as, but slightly larger than, a shape of inner shaft 168. Inner shaft 168 may translate relative to outer shaft 170. Outer shaft 170 may include indicia 146 to indicate insertion depth of end member 166 during use.

FIG. 8 depicts a perspective view of end member 166. A shape of end member 166 may be chosen to promote contact of rasp 164 with adjacent vertebrae. In some embodiments, a shape of end member 166 may be chosen to substantially match a shape of an implant. A cross-sectional shape of end member 166 may be, but is not limited to, oval, elliptical, circular, square, rectangular, or irregular. In certain embodiments, end member 166 may be kidney shaped. A height of end member 166 may be chosen to match a height of an implant to be inserted. For example, a height of end member 166 may be about 9 mm, about 11 mm, or about 13 mm. End member 166 may include opening 176. Inner shaft 168 may extend through opening 176 and couple with end member 166. End member 166 may include various configurations for coupling to inner shaft 168 (e.g., threads, pins, solder). For example, pin 178 may couple end member 166 to inner shaft 168.

Surfaces of end member 166 may be textured to abrade and/or cut vertebral bone. Texturing may be provided by methods including, but not limited to, sanding the surface, forming grooves in the surface, shot peening the surface, scoring the surface using an electrical discharge process, and/or embedding hard particles in the surface.

Rotation (e.g., clockwise rotation) of locking member 172 may allow outer shaft 170 to engage end member 166. In certain embodiments, rotation of locking member 172 may allow a biasing member to drive outer shaft 170 toward end member 166. The biasing member may be, but is not limited to, a spring, a spring mechanism, and/or an elastomer. Distal end 180 of outer shaft 170 may engage end member 166 to hold the end member in position at an initial angle relative to inner shaft 168. Distal end 180 may include various configurations (e.g., grooves and ridges, detents and indents, openings and protrusions, or threads) to engage end member 166. For example, edges of end member 166 and distal end 180 may include complementary ridges and grooves that engage when aligned. In other embodiments, end member 166 may include indents or slots that engage detents or pins of distal end 180. In certain embodiments, distal end 180 may include indents that engage detents of end member 166.

Rotation of locking member 172 in an opposite direction (e.g., counterclockwise) may release distal end 180 from end member 166. In certain embodiments, releasing locking member 172 may release a biasing member holding distal end 180 against end member 166. Release of the biasing member may release distal end 180 from end member 166. With distal end 180 released from end member 166, handle 174 may be used to pivot end member 166 relative to inner shaft 168. FIG. 9 depicts rasp 164 with end member 166 angled relative to inner shaft 168. After positioning of end member 166, locking member 172 may be engaged to secure a position of end member 166 relative to inner shaft 168. An angle of end member 166 relative to inner shaft 168 may be adjusted to range from about 0° to about 90°. In some embodiments, an angle of end member 166 relative to inner shaft 168 may be about 45° during use. In other embodiments, an angle of end member 166 relative to inner shaft 168 may be about 30° during use. In certain embodiments, an angle of end member 166 relative to inner shaft 168 may be about 60° during use. An angle of end member 166 relative to inner shaft 168 may allow rasp 164 to be inserted in a disc space during a transverse approach. After insertion, end member 166 may be pivoted to allow rasp 164 to be maneuvered in the disc space. End member 166 may be pivoted and locked in various angles relative to inner shaft 168 while in the disc space to abrade vertebral surfaces.

Rasp 164 may be advanced in a disc space to abrade vertebral surfaces. Abrasion of vertebral surfaces may be performed by moving handle 174 of rasp 164. Handle 174 may include grips and/or a textured surface. A proximal end of handle 174 may include an attachment for a drive instrument (e.g., a slap hammer). In certain embodiments, handle 174 may be removable from inner shaft 168 of rasp 164.

Figure 10:
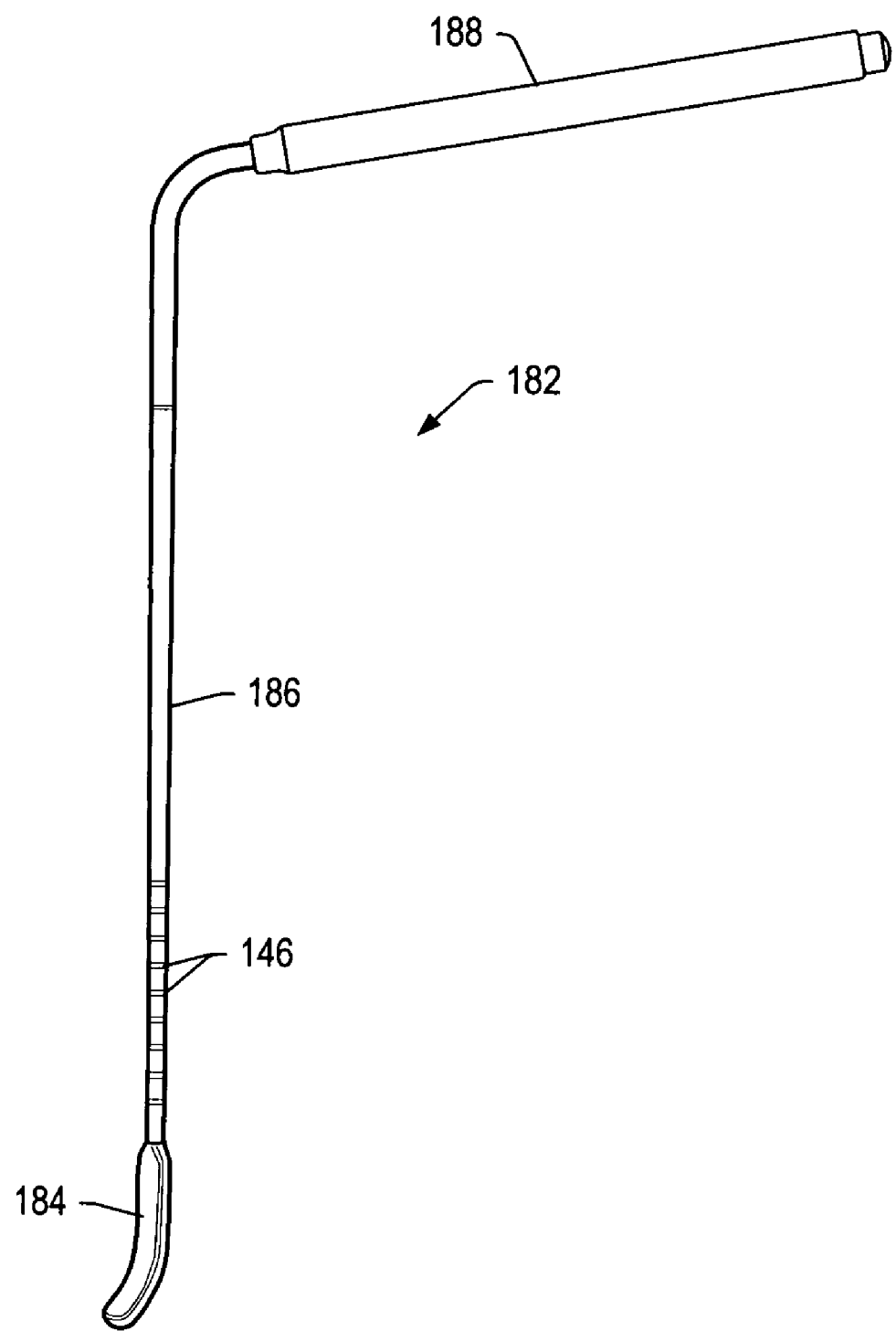
FIG. 10 depicts a perspective view of an embodiment of a guide.

An instrument guide may be used to facilitate positioning of an implant in a prepared disc space. FIG. 10 depicts a perspective view of an embodiment of instrument guide 182 that may be used to guide an implant in a disc space. Guide 182 may include end member 184, shaft 186, and handle 188. A height of end member 184 may complement a size of implant 100. A shape of end member 184 may be curved to help maneuver an implant in a disc space. In some embodiments, a cross-sectional shape of end member 184 may be curved.

End member 184 may couple to shaft 186. A height and shape of shaft 186 and handle 188 may facilitate positioning guide in a desired location while keeping the handle out of the way when end member 184 is properly positioned. Shaft 186 may be curved near handle 188 to enable an implant inserter and/or other instrument to be positioned proximate guide 182. Shaft 186 may include indicia 146 to indicate an insertion depth of end member 184.

An implant inserter may be used to position an implant in a disc space. In some embodiments, the implant inserter may be used to grasp side surfaces of an implant. An implant designed to be grasped from the side may have a solid end. An implant with a solid end may be structurally strong enough to withstand forces that may break or fracture implants with an opening in an end. The use of an implant inserter to grasp side surfaces of an implant may avoid application of rotational forces to the implant during removal of the implant inserter.

Figure 11:
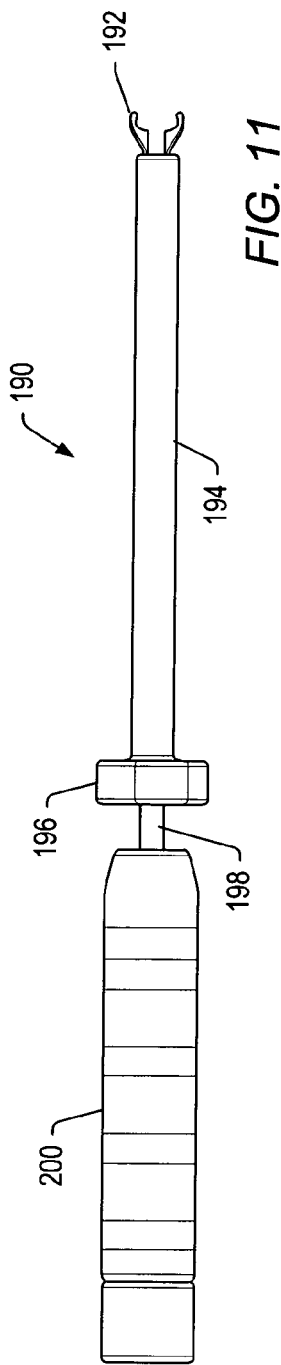
FIG. 11 depicts a front view of an embodiment of an implant inserter.

FIG. 11 depicts an embodiment of implant inserter 190 that may be used to insert implant 100 in a prepared disc space. Implant inserter 190 may advantageously have a low profile. An implant inserter with a low profile may allow a surgeon to see a surgical site during an implant insertion procedure. Implant inserter 190 may include arms 192, outer shaft 194, locking member 196, inner shaft 198, and handle 200. Arms 192 may couple to inner shaft 198. Outer shaft 194 may have a cross-sectional shape that is substantially the same as, but slightly larger than, a shape of inner shaft 198. Inner shaft 198 may rotate and/or translate in outer shaft 194. Inner shaft 198 may be fixed to handle 200. Proximal end of handle 200 may include an attachment for a drive instrument (e.g., a slap hammer) used during insertion of an implant in the disc space. In some embodiments, handle 200 may be removable from inner shaft 198.

Grasping portions of arms 192 of implant inserter 190 may be wider than other portions of the arms. Arms 192 may grasp recesses or grooves (e.g., grooves 120 of implant 100 depicted in FIG. 1) of an implant positioned between the arms. Arms 192 may be roughened, grooved, knurled, shot peened, chamfered, or otherwise textured to promote contact between the implant and the arms.

Figure 13A:
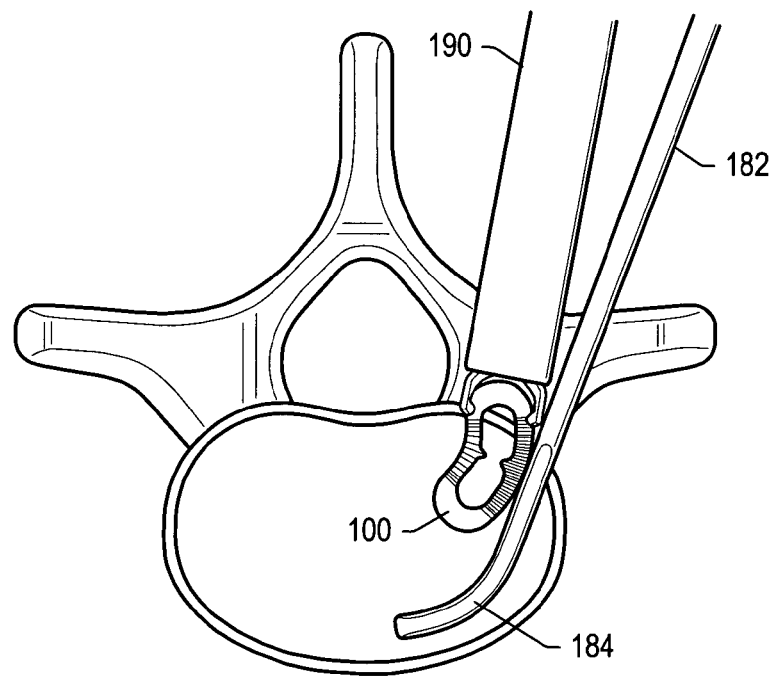
FIGS. 13A-13D depict schematic views during insertion of a spinal implant in a disc space.

Rotation (e.g., clockwise rotation) of locking member 196 may drive outer shaft 194 toward an implant positioned between arms 192. In certain embodiments, rotation of locking member 196 may allow a biasing member to drive outer shaft 194 toward an implant positioned between arms 192. An end of outer shaft 194 may contact wide portions of arms 192 to hold the implant between the arms, as depicted in FIG. 13A. Rotation of locking member 196 in an opposite direction (e.g., counterclockwise) releases outer shaft 194 and allows arms 192 to separate, thereby releasing the implant. In certain embodiments, rotation of locking member 196 may release a biasing member. Release of the biasing member may release outer shaft 194 and allow arms 192 to separate, thereby releasing the implant.

Figure 12:
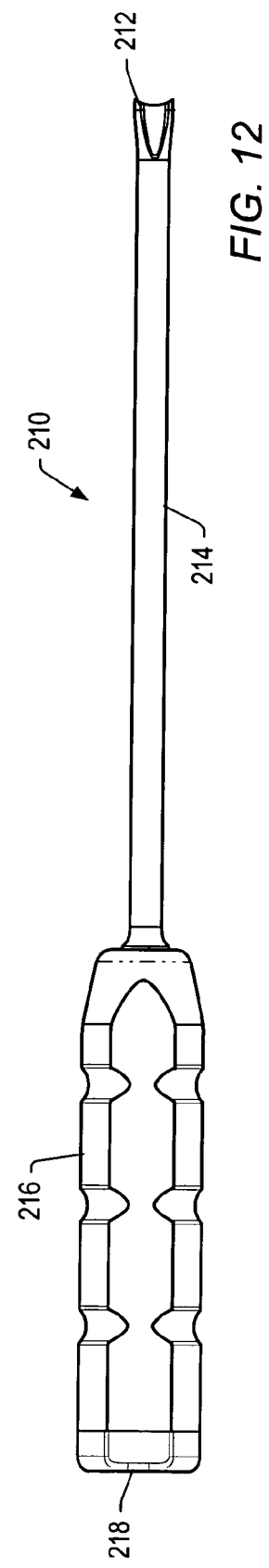
FIG. 12 depicts a front view of an embodiment of a guide.

After an implant has been released from implant inserter 190, instrument guide 210 may be used to position the implant. FIG. 12 depicts an embodiment of guide 210. Guide 210 may include tip 212, shaft 214, and handle 216.

A distal end of tip 212 may have a cross-sectional shape characterized by a narrow dimension and a wide dimension. The narrow dimension and the wide dimension may be substantially perpendicular to each other. Tip 212 may be tapered at the distal end in the narrow dimension. Tip 212 may be curved in the wide dimension. A curve in the wide dimension of the tip may complement a rounded edge of an implant. The curvature of tip 212 may be used to help guide the implant into position during a transverse approach.

Handle 216 may be coupled to shaft 214. The proximal end of handle 216 may include strike surface 218. A mallet or other impact tool may be used to hit strike surface 218 during insertion of an implant. Strike surface 218 may be located substantially directly over an implant to distribute a force across the implant surface. In some embodiments, a portion of strike surface 218 may be located above a corner of implant 100 to facilitate proper positioning of the implant during use.

A spinal implant may be inserted in an intervertebral disc space using a minimally invasive approach or a traditional surgical approach (e.g., transverse, posterior, anterior). A transverse approach may involve removal of a portion or the entire facet joint unilaterally. In some embodiments, a port may be inserted into a patient to provide access to vertebrae that are to be fused together. Instruments (e.g., distractors, chisels, size trials, implant inserters) may be inserted into the port during an implant insertion procedure.

Portions of bone and/or other material may be used to form a spinal implant designed to fuse two vertebrae together. The resulting implant may be provided with a desired lordotic angle and/or texturing that inhibits backout of an implant from a disc space. If an implant is formed of bone, the implant may be processed in a freeze-dried state. Before insertion into a patient, a freeze-dried implant may be reconstituted by soaking the implant in an aqueous solution.

During an insertion procedure, disc material may be removed to form a disc space. An implant may be inserted in the disc space. In a posterior procedure, an incision may be made and portions of a lamina or spinous process may be removed to provide access to the disc. The spinal cord or cauda equina may be retracted.

In a transverse approach, a portion of a facet joint may be removed. An implant that spans an intervertebral disc space may be inserted in the disc space. Insertion of an implant using a transverse approach may maintain healthy anatomical structure of the vertebrae on the contralateral side. In some embodiments a pedicle screw and rod construct may be applied to the same side or on opposite sides of an implant to strengthen the implant.

A discectomy may be performed to remove disc material from a disc space. A distractor, such as distractor 134 depicted in FIG. 4, may be positioned in the disc space to establish a separation distance between the vertebrae. A disc space may be prepared using instruments such as, but not limited to, curettes, chisels, or rongeurs. A chisel may be used to remove portions of vertebral bone and form channels in the vertebral end plates adjacent to the disc space.

A rasp, such as rasp 164 depicted in FIG. 7, may be used to remove disc material and roughen the vertebral endplates, allowing for improved vascularity of the bony mass. End member 166 may be angled relative to inner shaft 168 of rasp 164 in the disc space to prepare the disc space from a unilateral approach. A size of rasp 164 may be used to select a size of an implant to be inserted.

Figure 13B:
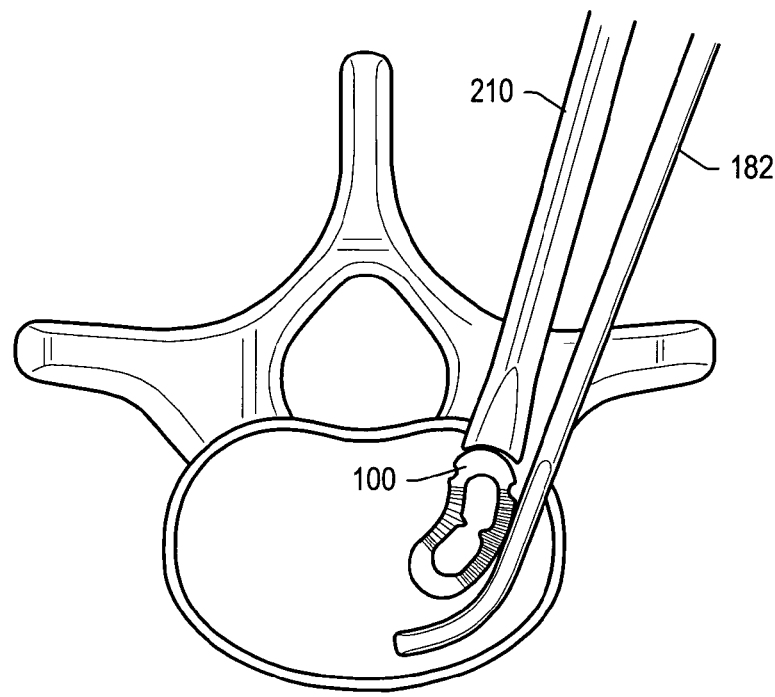
Figure 13C:
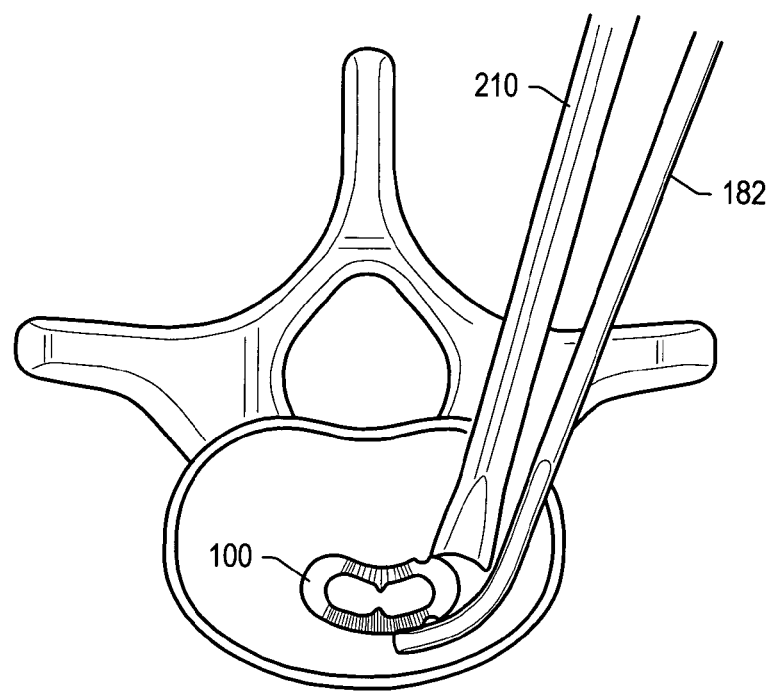

FIGS. 13A-13C depict insertion of implant 100 in a prepared disc space. An implant, such as implant 100 depicted in FIGS. 1-3, may be attached to an implant inserter, such as implant inserter 190 depicted in FIG. 11. A guide, such as guide 182 depicted in FIG. 10, may be inserted in the prepared disc space. In some embodiments, a portion of guide 182 may be equal in size to implant 100. Implant 100 may be placed proximate guide 182, as depicted in FIG. 13A. Implant 100 may be positioned along end member 184 of guide 182 until the implant is proximate the curved portion of the end member. Implant 100 may be released from implant inserter 190.

Figure 13D:
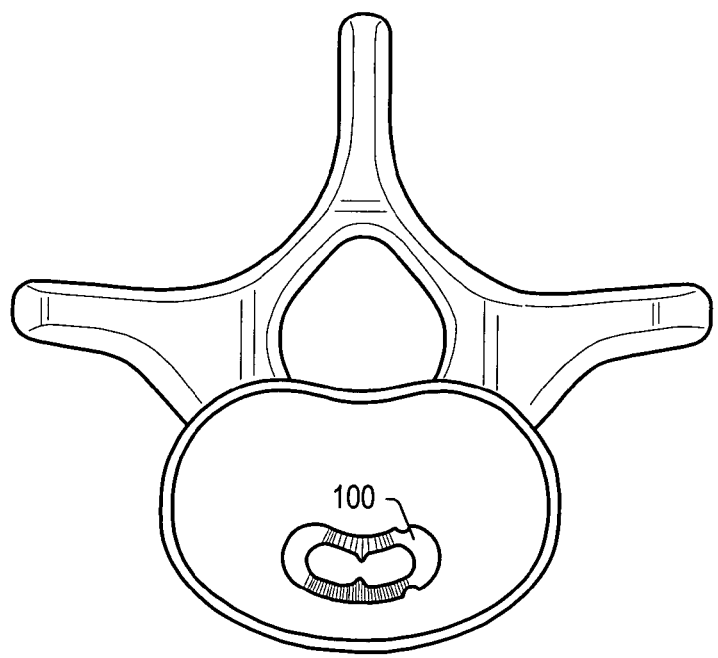

A guide, such as guide 210 depicted in FIG. 12, may be inserted into the disc space. Guide 210 may be placed proximate a proximal end of implant 100 as depicted in FIG. 13B. As shown in FIG. 13C, guides 210, 182 may be used in concert to guide, turn, and/or position implant 100 in the prepared disc space. A strike instrument may be used with guide 210 to move the implant along end member 184 of guide 182. FIG. 13D depicts implant 100 after removal of the guides from the disc space.

In this patent, certain U.S. patents have been incorporated by reference. The text of such U.S. patents is, however, only incorporated by reference to the extent that no conflict exists between such text and the other statements and drawings set forth herein. In the event of such conflict, then any such conflicting text in such incorporated by reference in such U.S. patents is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A spinal implant, comprising:
   a distal end;
   a proximal end opposite the distal end;
   a top extending between the distal end and the proximal end, wherein at least a portion of the top is shaped to contact a first vertebra;
   a bottom extending between the distal end and the proximal end opposite the top, wherein at least a portion of the bottom is shaped to contact a second vertebra, wherein the second vertebra is adjacent to the first vertebra;
   an anterior side extending between said top and said bottom and having:
      a first curvature between the distal end and the proximal end of said spinal implant; and
      a first groove located on the first curvature near said proximal end and extending from and passing through said top to said bottom;
   a posterior side extending between the top and the bottom opposite said anterior side and having:

a second curvature between said distal end and said proximal end of said spinal implant; and a second groove located on the second curvature near said proximal end and extending from and passing through said top to said bottom, wherein said first groove and said second groove are located substantially equidistant from said proximal end, wherein the first curvature and the second curvature are substantially in the same direction; and an opening extending through the spinal implant from the top to the bottom.

2. The spinal implant of claim 1, wherein the proximal end is substantially flat.

3. The spinal implant of claim 1, wherein the proximal end is substantially rounded.

4. The spinal implant of claim 1, wherein the distal end is tapered.

5. The spinal implant of claim 1, wherein the distal end is curved.

6. The spinal implant of claim 1, wherein the top comprises one or more protrusions configured to contact the first vertebra.

7. The spinal implant of claim 1, wherein the top comprises protrusions configured to contact the first vertebra, and wherein at least two of the protrusions differ in height, shape, or both.

8. The spinal implant of claim 1, wherein the top comprises protrusions configured to contact the first vertebra, and wherein the protrusions are in a radial pattern.

9. The spinal implant of claim 1, wherein the top comprises protrusions configured to contact the first vertebra, and wherein a first spacing between a first pair of adjacent protrusions differs from a second spacing between a second pair of adjacent protrusions.

10. The spinal implant of claim 1, wherein the bottom comprises one or more protrusions configured to contact the second vertebra.

11. The spinal implant of claim 1, wherein the bottom comprises protrusions configured to contact the second vertebra, and wherein at least two of the protrusions differ in height, shape, or both.

12. The spinal implant of claim 1, wherein the bottom comprises protrusions configured to contact the second vertebra, and wherein the protrusions are in a radial pattern.

13. The spinal implant of claim 1, wherein the bottom comprises protrusions configured to contact the second vertebra, and wherein a first spacing between a first pair of adjacent protrusions differs from a second spacing between a second pair of adjacent protrusions.

14. The spinal implant of claim 1, wherein an inner surface of the anterior side comprises one or more projections extending into the opening, and wherein the one or more projections are configured to strengthen the implant.

15. The spinal implant of claim 1, wherein an inner surface of the posterior side comprises one or more projections extending into the opening, and wherein the one or more projections are configured to strengthen the implant 16. The spinal implant of claim 1, wherein the grooves are configured to engage an insertion instrument.

17. The spinal implant of claim 1, wherein the distal end comprises grooves configured to engage an insertion instrument.

18. The spinal implant of claim 1, further comprising one or more openings extending through the anterior side, the posterior side, or both the anterior side and the posterior side.

19. The spinal implant of claim 1, further comprising one or more openings extending through the anterior side and one or more openings extending through the posterior side, and wherein at least one of the anterior side openings aligns with at least one of the posterior side openings to allow for monitoring of bone growth through the implant.

20. The spinal implant of claim 1, wherein the spinal implant comprises bone.

21. The spinal implant of claim 1, wherein the spinal implant comprises polyether ether ketone.

22. The spinal implant of claim 1, wherein the spinal implant comprises one or more openings for X-ray sensitive material.

23. The spinal implant of claim 1, wherein the spinal implant comprises metal.

24. The spinal implant of claim 1, wherein the spinal implant comprises titanium.

25. The spinal implant of claim 1, wherein the top is treated to promote osseointegration of the implant with bone.

26. The spinal implant of claim 1, wherein the top is roughened to promote fusion of the spinal implant with bone.

27. The spinal implant of claim 1, wherein the opening is shaped to receive packing material.

28. The spinal implant of claim 1, further comprising packing material placed in the opening, and wherein the packing material comprises bone.

29. The spinal implant of claim 1, further comprising packing material placed in the opening, wherein the packing material comprises synthetic bone material.

30. The spinal implant of claim 1 wherein the first curvature is substantially similar to the second curvature.

31. The spinal implant of claim 1 wherein the first and second curvature form a substantially kidney-shaped cross-section.

32. A spinal implant, comprising:
a body, wherein the body comprises:
a distal end;
a proximal end opposite the distal end;
a top extending between the distal end and the proximal end and comprising radially positioned top protrusions, wherein the top protrusions are shaped to contact a first vertebra;
a bottom extending between the distal end and the proximal end opposite the top and comprising radially positioned bottom protrusions, wherein the bottom protrusions are shaped to contact a second vertebra, wherein the second vertebra is adjacent to the first vertebra;
a curved anterior side between said top, said bottom, the distal end, and the proximal end of said body;
a curved posterior side opposite said curved anterior side and between said top, said bottom, said distal end, and said proximal end, wherein a cross-section formed by the anterior side and the posterior side is substantially kidney-shaped;
two grooves recessing into said body and passing through from said top to said bottom on said anterior side and said posterior side, wherein said two grooves are located substantially equidistant from said proximal end; and
an opening extending through the body from the top to the bottom.

33. The spinal implant of claim 32, wherein the top protrusions near the anterior side are coarser than the top protrusions near the posterior side.

34. The spinal implant of claim 32, wherein the bottom protrusions near the anterior side are coarser than the bottom protrusions near the posterior side.

35. The spinal implant of claim 32, wherein at least two of the top protrusions differ in height, shape, or both.

36. The spinal implant of claim 32, wherein a first spacing between a first pair of adjacent top protrusions differs from a second spacing between a second pair of adjacent top protrusions.

37. The spinal implant of claim 32, wherein at least two of the bottom protrusions differ in height, shape, or both.

38. The spinal implant of claim 32, wherein a first spacing between a first pair of adjacent bottom protrusions differs from a second spacing between a second pair of adjacent bottom protrusions.

39. The spinal implant of claim 32, wherein the top protrusions near the posterior side of the body are larger than the top protrusions near the anterior side of the body.

40. The spinal implant of claim 32, wherein the top protrusions near the posterior side of the body are higher than the top protrusions near the anterior side of the body.

41. The spinal implant of claim 32, wherein the bottom protrusions near the posterior side of the body are larger than the bottom protrusions near the anterior side of the body.

42. The spinal implant of claim 32, wherein the bottom protrusions near the posterior side of the body are higher than the bottom protrusions near the anterior side of the body.

43. A spinal implant, comprising:
a body, wherein the body comprises:
  a distal end;
  a proximal end opposite said distal end;
  a curved anterior side between said distal end and said proximal end;
  a curved posterior side opposite said curved anterior side and between said distal end and said proximal end;
  a top extending between the distal end and the proximal end and comprising top protrusions near said anterior side and said posterior side, wherein the top protrusions near the anterior side are finer than the top protrusions near the posterior side;
  a bottom extending between the distal end and the proximal end opposite said top;
  two grooves recessing into said body and passing through from said top to said bottom on said anterior side and said posterior side, wherein said two grooves are located substantially equidistant from said proximal end; and
  an opening extending through the body from the top to the bottom,
wherein the body is substantially kidney shaped.

44. The spinal implant of claim 43, wherein the bottom further comprises bottom protrusions near said anterior side and said posterior side, and wherein the bottom protrusions near the anterior side are finer than the bottom protrusions near the posterior side.

45. The spinal implant of claim 43, wherein the bottom further comprises bottom protrusions near said anterior side and said posterior side, and wherein the bottom protrusions near the anterior side are coarser than the bottom protrusions near the posterior side.

46. The spinal implant of claim 43, wherein the bottom further comprises bottom protrusions, wherein the bottom protrusions near the anterior side comprise a first radial pattern, and wherein the bottom protrusions near the posterior side comprise a second radial pattern.

47. The spinal implant of claim 43, wherein the top protrusions near the anterior side comprise a radial pattern.

48. The spinal implant of claim 43, wherein the top protrusions near the posterior side comprise a radial pattern.

49. The spinal implant of claim 43, further comprising one or more openings extending through the anterior side, the posterior side, or both the anterior side and the posterior side.

50. The spinal implant of claim 43, further comprising one or more openings extending through the anterior side and one or more openings extending through the posterior side, and wherein at least one of the anterior side openings aligns with at least one of the posterior side openings to allow monitoring of bone growth through the body.

* * * * *